United States Patent [19]

Hewitt

[11] 4,250,383
[45] Feb. 10, 1981

[54] THREAD INSPECTION APPARATUS AND METHOD

[76] Inventor: Burton L. Hewitt, 704 Oxford Dr., Laurel, Miss. 39440

[21] Appl. No.: 75,733

[22] Filed: Sep. 14, 1979

[51] Int. Cl.³ .............................................. G09K 3/00
[52] U.S. Cl. .................................... 250/302; 250/365
[58] Field of Search ............... 250/302, 361, 365, 461, 250/483, 484; 356/237

[56] References Cited

U.S. PATENT DOCUMENTS

| | | | |
|---|---|---|---|
| 2,217,991 | 10/1940 | Peck et al. | 250/483 |
| 2,649,500 | 8/1953 | Fedorchak | 250/365 |
| 3,417,241 | 12/1968 | Davis | 250/302 |

Primary Examiner—Bruce C. Anderson
Attorney, Agent, or Firm—Wigman & Cohen

[57] ABSTRACT

A method of and apparatus for inspecting the threads of tubular elements for flaws, cracks and the like are disclosed. The invention is particularly useful in performing thread inspections of the box and pin ends of drill collars according to known processes using a fluorescent solution and ultraviolet radiant energy. An inspection unit is provided which encloses the threads to be inspected in a light-excluding manner and houses a source of ultraviolet energy. The threads are visually inspected through an aperture in the inspection unit by either rotating the inspection unit or the tubular element to be inspected.

14 Claims, 7 Drawing Figures

THREAD INSPECTION APPARATUS AND METHOD

BACKGROUND OF THE INVENTION

The present invention relates to flaw detection methods and apparatus and, more particularly, to a method and apparatus for inspecting the threads of the pin and box ends of drill collars, drill pipe and the like for defects.

A search of the prior art failed to uncover any prior art reference which discloses the flaw detection method and apparatus of the present invention. Several prior art patents were uncovered which disclose various devices for inspecting the interior of hollow or tubular members as exemplified by the following U.S. Patents:

U.S. Pat. No. 3,371,176
U.S. Pat. No. 3,541,976
U.S. Pat. No. 2,682,032
U.S. Pat. No. 3,285,122

In the oil and gas well drilling arts, the drill string used for boring the well is made up of a heavy drill bit and a number of drill collars, reamers and stabilizers threaded together in end-to-end relation. Because of the heavy stresses placed on the threaded joints between each of these elements during drilling, as well as the high fluid pressures in the borehole and within these drilling elements, it is important to periodically check the integrity of the threads of each box and pin as the drill collars and other drill elements are made up and run into the hole or as they are pulled from the hole. Weekly inspections or inspections approximately every 200 hours are not an uncommon requirement.

Failure of a threaded joint during drilling is, of course, costly and time-consuming since it requires interruption of drilling to pull the entire drill string from the borehole and replace the defective drill collar or other defective element of the drill string.

It is known in the drilling art to perform nondestructive inspection of the threads at the ends of drill collars and drill pipe sections at the well drilling site. One method frequently employed for performing such inspection is known as the "ZYGLO" or "blacklight" process described, for example, in U.S. Pat. No. 2,259,400, the details of which are incorporated herein by reference. Generally speaking, this process involves treating the thread surfaces with a fluorescent solution which penetrates flaw openings. The fluorescent solution is then wiped from the surfaces to be inspected and when such surfaces are exposed to ultraviolet radiant energy, any fluorescent solution seeping from the flaw openings exhibits a distinctive and vivid appearance from normal surfaces without flaws.

In the field, the most common technique for performing this inspection process is to spray, brush or otherwise coat the pin and box end thread surfaces of the drill collar with a fluorescent solution and, thereafter, wipe away the excess. The person performing the inspection then drapes a dark cloth, such as a black blanket, over himself and the end of the drill collar to be inspected. Using a portable ultraviolet or "black light" held in one hand, the inspector visually observes all the threaded surfaces of the pin and box ends of the drill collar. This inspection procedure is not only disadvantageously inefficient, cumbersome and time-consuming, but is a rather unpleasant task for the inspector, particularly when the inspection is performed in the field during hot weather.

SUMMARY AND OBJECTS OF THE INVENTION

In view of the foregoing limitations of the known processes and devices for detection of flaws in the threads of drill collars and the like, as well as other disadvantages not specifically mentioned above, it should be apparent that there still exists a need in the art for a method and apparatus for rapidly performing flaw inspections of drill collar threads which eliminates the cumbersome and time-consuming conventional inspection methods.

It is, therefore, a primary object of this invention to fulfill this need by providing a self-contained inspection unit, including an ultraviolet light source, which unit is adapted to enshroud the threaded end of a drill collar and by providing a method of using such inspection unit to perform a complete 360° inspection of the drill collar threads in a particularly efficient manner.

More particularly, it is an object of this invention to provide a pair of special inspection units, each including a shroud-like housing or enclosure adapted to rotatably engage a respective pin or box end of a drill collar in a substantially light-excluding manner to permit simultaneous inspection of the threads at both ends of the drill collar. The housing of each inspection unit is provided with a visual inspection aperture and an integrally mounted ultraviolet light holder for performing flaw detection procedures using a fluorescent penetrant solution as previously described. An air source provides a stream of air for blowing away excess fluorescent solution to enhance the flaw detection capability of the process.

It is another object of the present invention to provide a self-contained flaw detection apparatus for use in the inspection of drill collars in situ at the drilling rig or at drill collar storage racks with the drill collars stored horizontally, which apparatus can be easily and readily manipulated to perform the necessary thread inspection in a rapid and efficient manner and with a minimum of training of the inspector.

Yet another object of this invention is to provide an improved method of detecting flaws in the threads of drill collars and pipe joints in the field from the standpoint of efficiency and economy.

Another object of the invention is to provide a flaw detection apparatus for the threaded ends of drill collars which apparatus is adapted to accommodate a large range of drill collar diameters, for example, from 4" to 11" diameter drill collars.

Briefly described, the aforementioned objects are accomplished according to the invention by providing a pair of inspection units, each of which is especially adapted to enclose a respective pin end or box end of a drill collar. The box end inspection unit comprises an opaque, lightweight plastic or sheet metal enclosure or housing which is adapted to be arranged about the box end of the drill collar in such manner as to substantially exclude light from the interior of the housing. A plurality of horizontal rollers and spring-biased centering arms are mounted within the housing so as to rotatably engage the ring-shaped annular end surface and peripheral surface, respectively, of the box end in turret-like fashion.

An ultraviolet light source, preferably battery-powered, is mounted in the housing with the axis of the light source oriented at an angle to the rotational axis of the inspection unit in such manner that the ultraviolet radiation floods the internal threads of the box end of the drill collar. An elongated reflective element, such as a metallic mirror, is pivotally mounted within the enclosure and is arranged to extend into the box end of the drill pipe substantially to the maximum depth of the box end threads. A shrouded inspection aperture is arranged in the housing wall generally opposite the reflective element through which aperture the reflected image of the threads is viewed after application of the fluorescent solution thereto.

The inspection unit is provided with a pair of oppositely disposed handles to permit manual rotation of the unit in a manner similar to a periscope so that a complete 360° inspection of the box end threads may be performed. At least one of the handles is equipped with a hollow, flexible bulb which is connected to a perforated air tube arranged to extend into the box end of the drill collar. When the bulb is squeezed, air is forced from the perforations in the air tube and blows excess fluorescent solution from the thread area under inspection.

The pin end inspection unit has a simpler construction than the box end unit but is intended to perform the same general functions of the box end unit. No reflective element is required in the pin end unit since the threads are external and may be directly viewed through a shrouded inspection aperture in the pin end unit housing.

According to the method of the present invention, the pin and box end threads of a drill collar are inspected for flaws with the drill collars arranged vertically in their conventional orientation, i.e., box end up and pin end down. In one aspect of the method, the inspection is performed during make-up or break-out of the drill collar sections at the rotary table of the drilling rig.

The method of the present invention also contemplates the inspection of drill collar threads with the drill collars arranged horizontally on racks adjacent the drilling rig or at a tool storage site. In these circumstances, the inspection is preferably carried out simultaneously by two inspectors, each one of whom operates a respective inspection unit. The inspection units are arranged about the ends of the horizontally disposed drill collar and the drill collar is rolled on the rack through 360° while the inspector maintains the inspection unit in a fixed orientation.

With these and other objects, advantages and features of the invention that may become hereinafter apparent, the nature of the apparatus and method of the invention may be more clearly understood by reference to the following detailed description thereof, the appended claims and to the several views illustrated in the attached drawings, wherein:

DETAILED DESCRIPTION OF A PREFERRED EMBODIMENT

Figure 1:
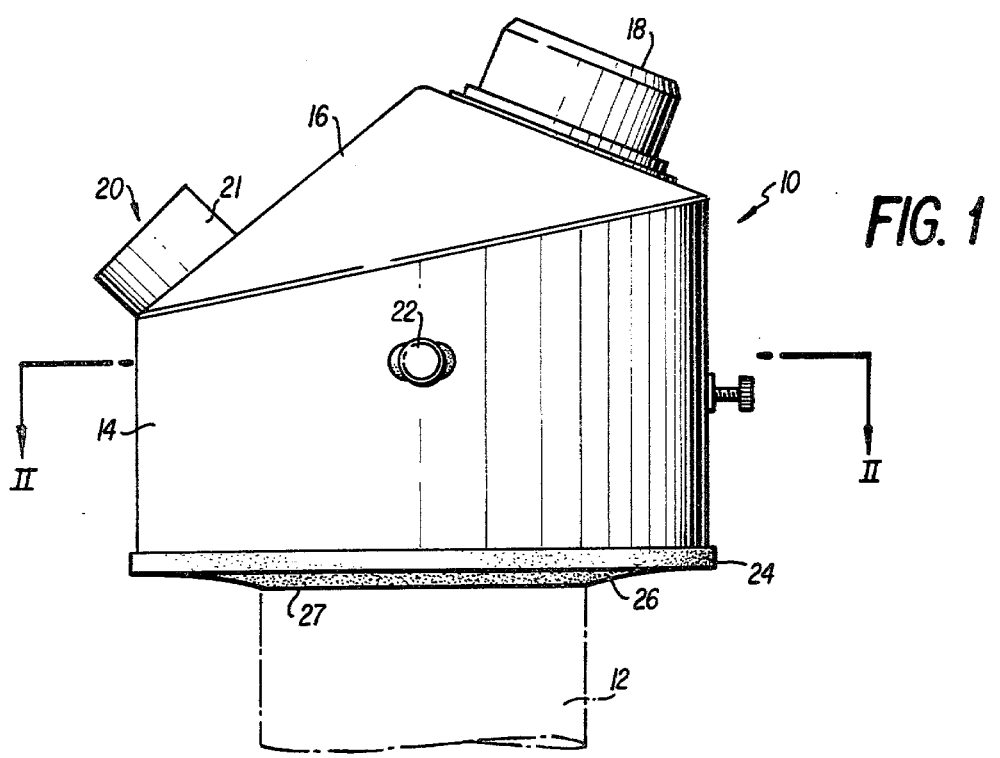
FIG. 1 is a side elevation view of the box end inspection unit of the apparatus of the present invention.

Referring now in detail to the drawings, there is shown in FIG. 1 a thread inspection unit constructed according to the present invention and designated generally by reference numeral 10. Unit 10 is especially adapted for inspecting the internal threads of the box end 12 of a drill collar section and comprises a lightweight, opaque plastic or sheet metal housing 14 of generally cylindrical configuration for enclosing the box end of the drill collar. The housing 14 is constructed in accordance with the invention to rotate in turret-like fashion about the box end 12 of the drill collar as more fully shown and described hereinafter in connection with FIGS. 2–4.

Housing 14 includes a top cover 16 in which is mounted an ultraviolet light source 18, which is preferably battery-powered. A visual inspection aperture 20 is provided in the wall of housing 14 through which the operator or inspector views and inspects the drill collar threads for flaws. The inspection aperture 20 is provided with an elastomeric viewing shroud or shield 21 to minimize the entry of ambient light into the interior of the inspection unit 10 and thereby improve the reliability of the inspection.

Handles 22, 22' (only one shown in FIG. 1) are mounted on opposite sides of the housing 14 and are adapted to be grasped by the inspector for rotating the housing through 360° in periscope-like manner according to one aspect of the method of the invention. According to another aspect of the method invention, the handles are grasped by the inspector so as to maintain the inspection unit in a fixed orientation while the drill collar 12 is rotated.

Secured to the lower skirt 24 of the housing 14 is a flexible, opaque sheet 26 which may be formed of a rubber material. Sheet 26 has a central opening 27 which fits snugly about the periphery of box end 12 of the drill collar. This snug-fitting relation will substantially exclude any ambient light from entering via the bottom of the housing 14 so as to improve the light contrast conditions within the housing thereby enhancing visual detection of flaws. If the skirt 24 is sufficiently long it may be unnecessary to utilize the sheet 26 to obtain adequate darkness within the housing for performing the inspection.

Now referring in greater detail to FIGS. 2–5, the operation of the box end inspection apparatus of FIG. 1 will be more clearly understood in conjunction with the previously mentioned "ZYGLO" flaw detection process described in U.S. Pat. No. 2,259,400. Mounted to the interior of the housing 14 are four radially arranged roller mounts 28 spaced 90° apart. A cylindrical roller 30 is rotatably supported on each roller mount by means of a shaft 32 or other suitable journalling means. The rollers 30 are adapted to bear upon the upper annular surface 34 of the box end of the drill pipe section to thereby provide for relative rotation between the inspection unit 10 and the box end of the drill collar.

Also arranged on the interior wall of the housing 14, are three arms 36 spaced 120° apart, to facilitate centering of the inspection unit 10 coaxially with the drill collar axis. The arms 36 are pivotably mounted to the housing between a pair of lugs 38 by a pin 39 and are inwardly biased by means of coil springs 40. It will be appreciated that other resilient biasing means may be employed, such as leaf or blade springs, elastomeric materials or the like.

The free ends 42 of the arms 36 are preferably rounded and smooth to minimize the frictional drag between the ends 42 and the peripheral surface of the box end 12 of the drill collar. If necessary or desirable, the free ends of the arms may be coated with a material having a low coefficient of friction or may be provided with a rolling surface, such as a ball roller or the like.

An elongated reflective element 44, for example, a metallic mirror, is mounted in a holder piece 46 which is pivotably affixed by a pin 48 to a bracket 50 extending radially inwardly from the interior wall of the housing 14. A threaded adjustment screw 52 extends through a threaded bushing 54 mounted in the cylindrical wall of the housing 14 and is connected to the holder piece 46 by a pin 56. Adjustment of the angle of the mirror 44 relative to the inspection aperture 20 to improve or vary the reflected field of vision of the inspector, is thus accomplished by rotating adjustment screw 52.

Figure 2:
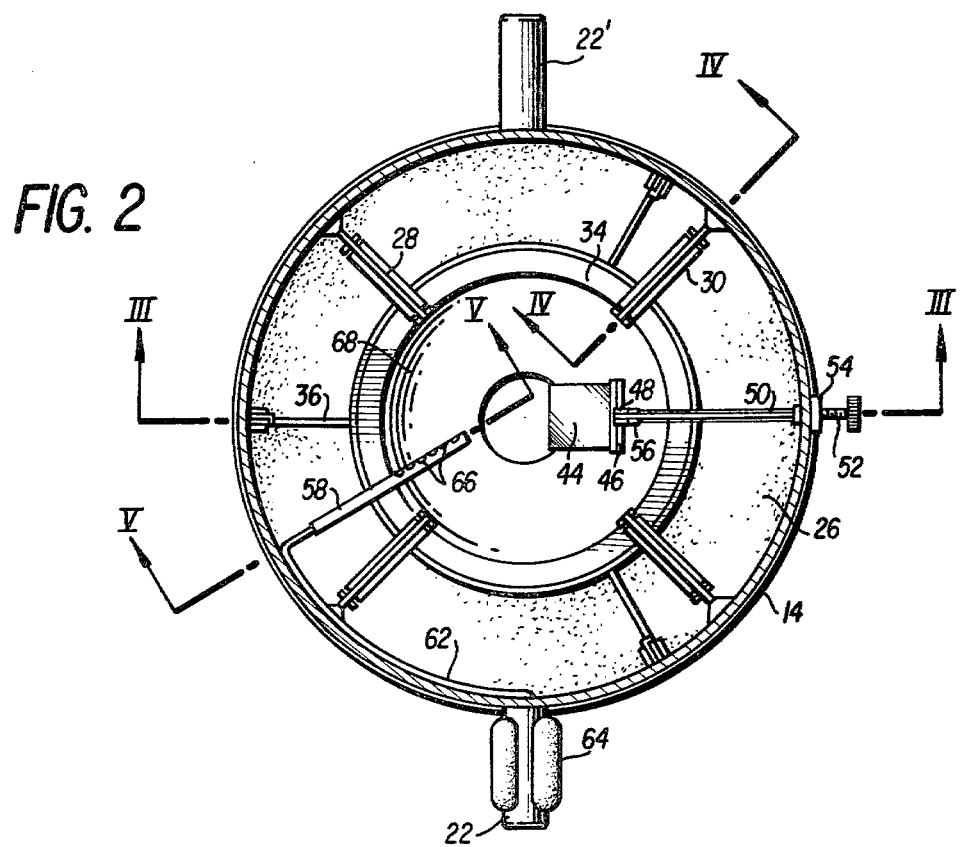
FIG. 2 is a cross-sectional view of the box end inspection unit taken along line II—II of FIG. 1.
Figure 5:
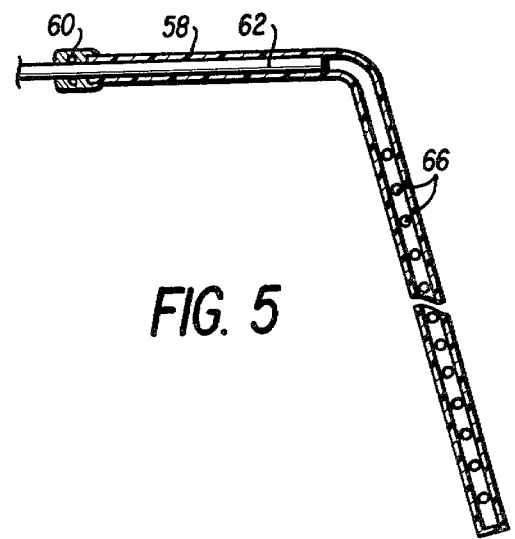
FIG. 5 is a fragmentary cross-sectional view of the perforated air tube taken along line V—V of FIG. 2.

As shown in FIGS. 2 and 5, a perforated air tube 58 is slidably arranged on the end of a rigid air pipe 62 extending radially from the wall of housing 14 toward the center thereof. An O-ring 60 forms a sliding seal between the perforated air tube and air pipe 62. The air pipe 62 extends from the perforated air tube along the interior wall of the housing to a point adjacent handle 22 where it is connected to a flexible, hollow air bulb 64 mounted in the handle 22. By squeezing bulb 64, air is forced from the bulb through air pipe 62 into perforated air tube 58 from where it is expelled through the perforations 66 in the tube 58 to blow away any excess fluorescent solution which may be present on the threads 68 in the box end 12 of the drill collar. Air tube 58 may be adjusted radially inwardly or outwardly along air pipe 62 to accommodate various diameter drill collars.

Figure 3:
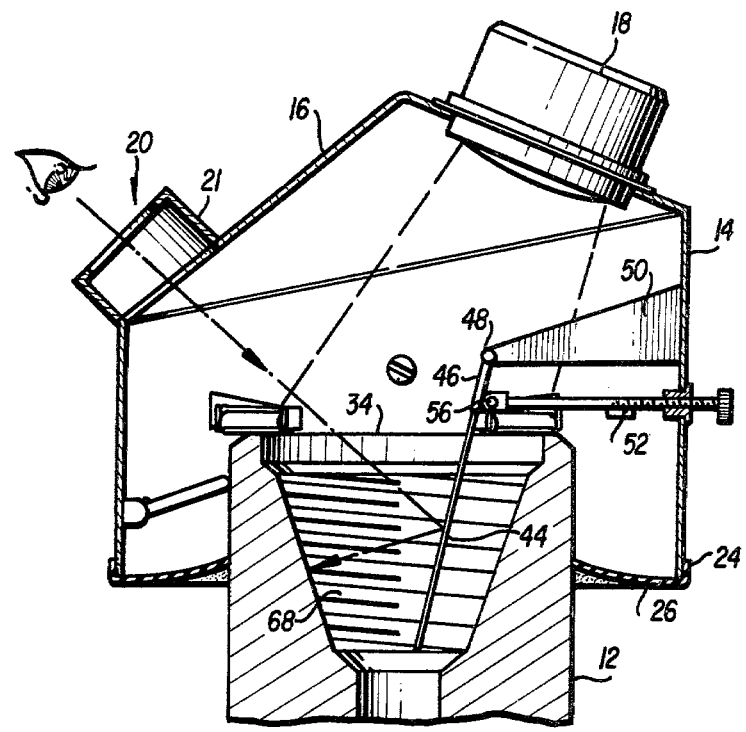
FIG. 3 is a cross-sectional view of the box end inspection unit of the present invention taken along the line III—III of FIG. 2.
Figure 4:
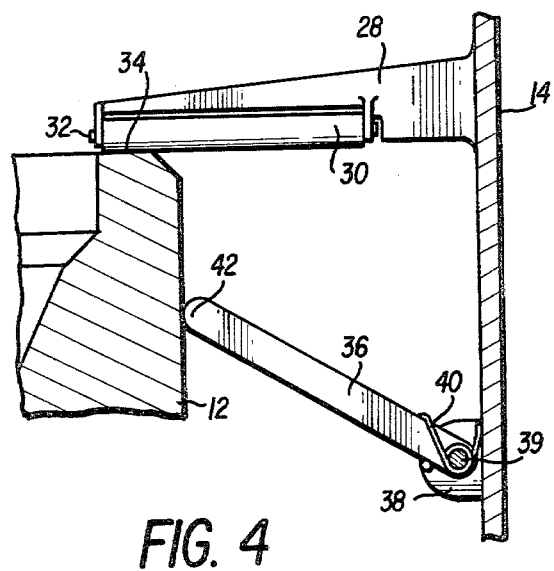
FIG. 4 is a fragmentary cross-sectional view of the roller mounting for the box end inspection unit taken along line IV—IV of FIG. 2.

Referring now to FIG. 3, the method of using the box end inspection unit 10 to inspect the box end of a vertically oriented drill collar will be described. First, a solution containing a fluorescent penetrant agent as in the "ZYGLO" process is sprayed or brushed on the threads 68 of the box end 12. The inspection unit 10 is then placed over the box end such that it is centered and rotatably supported on the end surface 34 by means of the rollers 30. The inspector then energizes the battery-powered ultraviolet source 18 to flood the interior of the inspection unit 10 with ultraviolet radiant energy and peers through the aperture 20 at the reflected image of threads 68 on mirror 44.

Excess fluorescent solution on the threads 68 is blown away from the inspection area by pumping the air bulb 64 in handle 22. Any agent seeping from cracks or other flaws in the threads will exhibit a vivid and distinctive fluorescence when exposed to the ultraviolet light energy. Using the handles 22, 22', the inspector rotates the inspection unit gradually, in periscope fashion, and observes the entire vertical extent of the reflected image of the threads through a complete 360° revolution of the inspection unit. When the inspection is completed, the unit 10 is simply lifted from the box end 12 of the drill collar.

Figure 6:
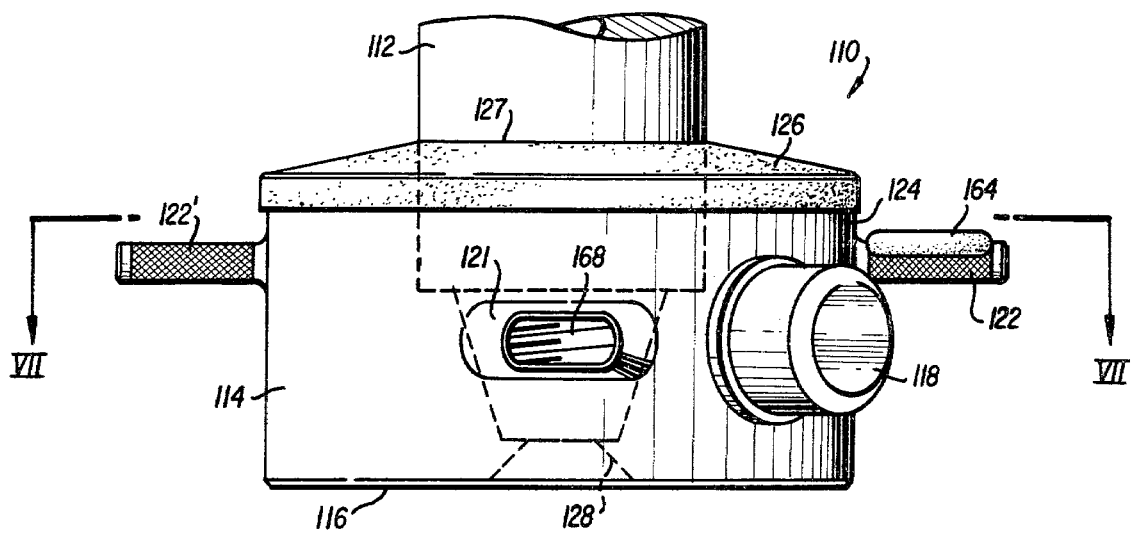
FIG. 6 is a side-elevation view of the pin end inspection unit of the present invention.
Figure 7:
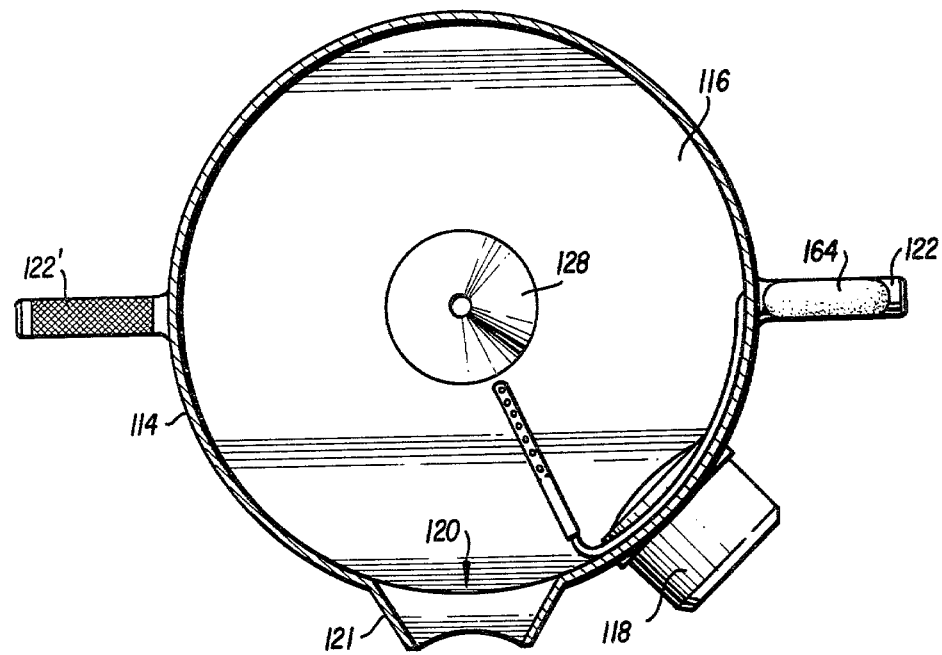
FIG. 7 is a cross-sectional view of the pin end inspection unit of the invention taken along line VII—VII of FIG. 6.

Inspection of the pin end of the drill collar is performed with the inspection unit 110 shown in FIGS. 6 and 7. Unit 110 comprises a cylindrical housing 114 including end cover 116 adapted to enclose the pin end 112 of a drill collar or the like. Housing 114 and end cover 116 are constructed preferably of a lightweight, opaque plastic material or of thin sheet metal.

Affixed to the upper circumferential edge 124 of the housing is a flexible sheet 126 having a central opening 127 through which the pin end 112 of the drill collar is inserted. Sheet 126 functions in the same manner as sheet 26 of the box end inspection unit 110 to exclude light from the interior of the inspection unit. An ultaviolet light source 118 is mounted in the wall of housing 114 adjacent an inspection aperture 120 which is surrounded by a viewing shroud or shield 121. A pair of handles 122, 122' are mounted on opposite sides of the housing 114 for operating the pin end inspection unit in the same manner as box end unit 10.

The pin end unit 110 is centered on the drill collar 112 by means of a conical guide 128 centrally arranged on end cover 116. Guide 128 engages in the inside diameter of the drill collar and, together with the sheet 126 which engages the outside of the pin end 112, aids in maintaining the unit 110 coaxial or centered with the drill collar axis. The conical shape of the guide permits it to be used with all the drill collar diameters for which the inspection unit is designed. If the end cover 116 is molded of a plastic material, the conical guide 128 may be integrally formed in the cover according to well-known molding methods.

Pin end inspection unit 110 is also provided with a perforated air tube 158 of similar construction as tube 58 except that the perforations 166 (FIG. 7) are differently oriented so that the air expelled therefrom is directed onto the external pin end threads 168. Tube 158 is connected with an air pipe 162 and air bulb 164 mounted in handle 122 in the same manner as the corresponding elements of box end unit 10.

Operation of pin end inspection unit 110 is almost identical to that of unit 10 except that the pin end unit is engaged upwardly over the downwardly extending pin end of the drill collar and the pin end threads may be viewed directly, rather than indirectly by means of the reflected image as required in the box unit 10.

It would be possible, if desired, to modify the box and pin end inspection units to incorporate means for applying the fluorescent solution to the threads, for example, by a spray nozzle supplied by a source of the solution under pressure. Other variations will also be apparent to those skilled in the art, for example, supplying air for the perforated air tube from a pressurized air source.

When using the inspection units 10 and 110 at the drilling rig to perform in situ inspections of drill collar threads, for example, when the drill is being pulled from the borehole, the box end is inspected while it is still in the rotary table and the pin end of the drill collar just disengaged from such box end and hanging free of the rotary table is inspected. Thus, the inspector views the threads while standing upright adjacent the inspection apertures 20 and 120 in a position generally parallel to the drill collar axis. If two inspectors are employed, the inspections may be simultaneously performed each time a drill collar is spun out. The thread inspection may also be performed when the drill is going in the hole as well as when the drill is coming out of the hole.

If it is desired to perform an inspection of the threads of drill collars, drill tube sections or any other threaded tool, joint, sub or the like, which are arranged horizontally on racks as is common in the well drilling art, the inspection units 10 and 110 are readily employed for such inspections. In such case, two inspectors are preferred for performing the pin and box end inspections simultaneously.

The units 10 and 110 are engaged over the ends of the drill collar, drill tube or other threaded component to be inspected with the inspection apertures 20 and 120 directed generally upwardly. The inspectors take a position standing at the respective end covers 16 and 116 of the inspection units, generally at right angles to the axis of the drill collar to be inspected. In this case, the preferred method of inspecting the threads is for the inspectors to maintain the orientation of the inspection units 10 and 110 fixed while viewing downwardly through the inspection apertures 20 and 120. The drill collar is then rolled sideways on the rack through 360° while the inspectors perform the inspection.

While the material of the housings 14 and 114 has been disclosed above as plastic or sheet metal, a plastic material is greatly preferred for several reasons. For example, the likelihood of electrical shock in the event of short circuits involving a light source 18, 118 powered from a conventional 110-115 volt AC source is substantially eliminated. In addition, the overall weight of the inspection units can be minimized by the use of a plastic housing. For added durability, a fiberglass-reinforced plastic material is preferred.

Although only preferred embodiments of the invention are specifically illustrated and described above, it will be appreciated that many modifications and variations of the present invention are possible in light of the above teachings and within the purview of the appended claims without departing from the spirit and intended scope of the invention.

What I claim is:

1. Apparatus for inspecting threaded elements for flaws using radiant energy, especially the threaded box and pin ends of drill collars, drill tubing and other threaded tubular elements, comprising portable housing means for enclosing the threads to be inspected in a substantially light-excluding manner, said housing means including means cooperating with said threaded element for locating said housing means relative to said threaded element and for facilitating relative rotation therebetween, a source of ultraviolet energy supported by said housing means and oriented to direct ultraviolet energy upon the threads to be inspected, said housing means further including an inspection aperture through which the threads to be inspected are visually observed, said aperture having a field of view within the housing means.

2. Apparatus according to claim 1, wherein said housing means comprises an opaque housing member having two ends and an end cover disposed over one of said ends.

3. Apparatus according to claim 1, wherein said inspection aperture is provided with a light-excluding shield extending outwardly from the housing means.

4. In a method of inspecting the threads of box and pin ends of drill collars and tubing for cracks, flaws and defects comprising the steps of treating the threads by applying a fluorescent penetrant solution thereto, removing excess solution from the threads and directing ultraviolet radiant energy upon the threads to cause fluorescence of the solution seeping from the cracks, flaws and defects, the improvement comprising:

providing a portable inspection housing having an ultraviolet energy source and an inspection aperture and means to substantially exclude ambient light from the interior of the housing during inspection of the threads;

after application of the solution to the threads to be inspected, enclosing the respective box or pin end with the inspection housing in a light-excluding manner;

energizing the ultraviolet energy source to thereby flood the treated threads with ultraviolet rays; and visually inspecting the threads for flaws, cracks and defects through the inspection aperture.

5. The improvement according to claim 4, including the step of rotating the drill collar through at least 360° while manually maintaining the inspection housing rotationally fixed.

6. Apparatus for inspecting threaded elements for flaws using radiant energy, especially the threaded box and pin ends of drill collars, drill tubing and other threaded tubular elements, comprising housing means for enclosing the threads to be inspected in a substantially light-excluding manner, said housing means comprising an opaque housing member having two ends and an end cover disposed over one of said ends, said housing means including means cooperating with said threaded element for locating said housing means relative to said threaded element and for facilitating relative rotation therebetween, a source of ultraviolet energy supported by said housing means and oriented to direct ultraviolet energy upon the threads to be inspected, said housing means further including an inspection aperture through which the threads to be inspected are visually observed, said aperture having a field of view within the housing means and means arranged within said housing member for blowing air on the threads to be inspected, whereby inspection of the threads with said ultraviolet energy is facilitated.

7. Apparatus according to claim 6, wherein said air blowing means includes a perforated air tube connected to an air source, said air source comprising a hollow, flexible air bulb adapted to be manually compressed.

8. Apparatus for inspecting threaded elements for flaws using radiant energy, especially the threaded box and pin ends of drill collars, drill tubing and other threaded tubular elements, comprising housing means for enclosing the threads to be inspected in a substantially light-excluding manner, said housing means, comprising an opaque housing member having two ends and an end cover disposed over one of said ends, said housing means including means cooperating with said threaded element for locating said housing means relative to said threaded element and for facilitating relative rotation therebetween, a source of ultraviolet energy supported by said housing means and oriented to direct ultraviolet energy upon the threads to be inspected, said housing means further including an inspection aperture through which the threads to be inspected are visually observed, said aperture having a field of view within the housing means and reflective element means mounted within said housing member for reflecting the image of the threads to be inspected into the field of view of the inspection aperture.

9. Apparatus according to claim 8, including means operatively connected to said reflective element means for adjusting the position of said reflective element means relative to the inspection aperture.

10. Apparatus for inspecting threaded elements for flaws using radiant energy, especially the threaded box and pin ends of drill collars, drill tubing and other threaded tubular elements, comprising housing means for enclosing the threads to be inspected in a substantially light-excluding manner, said housing means including means cooperating with said threaded element for locating said housing means relative to said threaded element and for facilitating relative rotation therebetween, said locating and relative rotation means comprising a plurality of rollers mounted in said housing means so as to bear rotatively upon the threaded element to be inspected and a plurality of spring-biased arms mounted in said housing means so as to substantially center said housing means with respect to the axis of said threaded element, a source of ultraviolet energy supported by said housing means and oriented to direct ultraviolet energy upon the threads to be inspected, said housing means further including an inspection aperture through which the threads to be inspected are visually observed, said aperture having a field of view within the housing means.

11. Apparatus for inspecting threaded elements for flaws using radiant energy, especially the threaded box and pin ends of drill collars, drill tubing and other threaded tubular elements, comprising housing means for enclosing the threads to be inspected in a substantially light-excluding manner, said housing means comprising an opaque housing member having two ends and an end cover disposed over one of said ends, said housing means including means cooperating with said threaded element for locating said housing means relative to said threaded element and for facilitating relative rotation therebetween, said locating and relative rotation means comprising a conical element disposed in said end cover and extending inwardly of the housing member, said conical element being adapted to engage said threaded element so as to substantially center the housing member and permit rotation thereof relative to the axis of said threaded element, a source of ultraviolet energy supported by said housing means and oriented to direct ultraviolet energy upon the threads to be inspected, said housing means further including an inspection aperture through which the threads to be inspected are visually observed, said aperture having a field of view within the housing means.

12. Apparatus for inspecting threaded elements for flaws using radiant energy, especially the threaded box and pin ends of drill collars, drill tubing and other threaded tubular elements, comprising housing means for enclosing the threads to be inspected in a substantially light-excluding manner, said housing means comprising an opaque housing member having two ends, an end cover disposed over one of said ends and an opaque, flexible sheet connected to the other end of said housing member, said sheet having an opening disposed therein, said opening being adapted to receive the threaded element to be inspected in such manner that ambient light is substantially excluded from passing between the opening in said sheet and said threaded element, said housing means including means cooperating with said threaded element for locating said housing means relative to said threaded element and for facilitating relative rotation therebetween, a source of ultraviolet energy supported by said housing means and oriented to direct ultraviolet energy upon the threads to be inspected, said housing means further including an inspection aperture through which the threads to be inspected are visually observed, said aperture having a field of view within the housing means.

13. In a method of inspecting the threads of box and pin ends of drill collars and tubing for cracks, flaws and defects comprising the steps of treating the threads by applying a fluorescent penetrant solution thereto, removing excess solution from the threads and directing ultraviolet radiant energy upon the threads to cause fluorescence of the solution seeping from the cracks, flaws and defects, the improvement comprising:
providing an inspection housing having oppositedly disposed handles, an ultraviolet energy source, an inspection aperture and means to substantially exclude ambient light from the interior of the housing during inspection of the threads;
after application of the solution to the threads to be inspected, enclosing the respective box or pin end with the inspection housing in a light-excluding manner;
energizing the ultraviolet energy source to thereby flood the treated threads with ultraviolet rays;
visually inspecting the threads for flaws, cracks and defects through the inspection aperture; and
during said inspecting step, manually rotating the inspection housing by means of said handles through at least 360° while maintaining the drill collar rotationally fixed.

14. In a method of inspecting the threads of box ends of drill collars and tubing for cracks, flaws and defects comprising the steps of treating the threads by applying a fluorescent penetrant solution thereto, removing excess solution from the threads and directing ultraviolet radiant energy upon the threads to cause fluorescence of the solution seeping from the cracks, flaws and defects, the improvement comprising:
providing an inspection housing having an ultraviolet energy source and an inspection aperture and means to substantially exclude ambient light from the interior of the housing during inspection of the threads;
after application of the solution to the threads to be inspected, enclosing the box end with the inspection housing in a light-excluding manner;
energizing the ultraviolet energy source to thereby flood the treaded threads with ultraviolet rays; and
visually inspecting the threads for flaws, cracks and defects through the inspection aperture by inserting a reflecting means into the box end, reflecting the image of the threads toward the inspection aperture and visually inspecting the reflected image for flaws, cracks and defects.

* * * * *

UNITED STATES PATENT AND TRADEMARK OFFICE
CERTIFICATE OF CORRECTION

PATENT NO. : 4,250,383
DATED : February 10, 1981
INVENTOR(S) : BURTON L. HEWITT

It is certified that error appears in the above—identified patent and that said Letters Patent is hereby corrected as shown below:

Column 6, line 13, change "ultavio-" to -- ultravio- --.

After claim 14, add claim 15 as follows:

--15. Apparatus for inspecting threaded elements for flaws using radiant energy, especially the threaded box and pin ends of drill collars, drill tubing and other threaded tubular elements, comprising housing means for enclosing the threads to be inspected in a substantially light-excluding manner, said housing means comprising an opaque housing member having two ends and an end cover disposed over one of said ends, said housing member being formed of a lightweight, plastic material and including a pair of handles disposed on opposite sides of said housing member, said housing means including means cooperating with said threaded element for locating said housing means relative to said threaded element and for facilitating relative rotation therebetween, a source of ultraviolet energy supported by said housing means and oriented to direct ultraviolet energy upon the threads to be inspected, said housing means further including an inspection aperture through which the threads to be inspected are visually observed, said aperture having a field of view within the housing means.--

UNITED STATES PATENT AND TRADEMARK OFFICE
CERTIFICATE OF CORRECTION

PATENT NO. : 4,250,383

DATED : February 10, 1981

INVENTOR(S) : Burton L. Newitt

It is certified that error appears in the above—identified patent and that said Letters Patent is hereby corrected as shown below:

On the title page, "14 Claims" should read -- 15 Claims --.

Signed and Sealed this

Thirtieth Day of June 1981

[SEAL]

Attest:

RENE D. TEGTMEYER

Attesting Officer

Acting Commissioner of Patents and Trademarks